US00PP37112P2

(12) United States Plant Patent
Capo

(10) Patent No.: US PP37,112 P2
(45) Date of Patent: Nov. 25, 2025

(54) ***PETUNIA* PLANT NAMED 'KLEPH23557'**

(50) Latin Name: *Petunia hybrida*
Varietal Denomination: KLEPH23557

(71) Applicant: KLEMM + SOHN GMBH & CO. KG, Stuttgart (DE)

(72) Inventor: Antonella Capo, Latina (IT)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 18/789,116

(22) Filed: Jul. 30, 2024

(51) Int. Cl.
*A01H 5/02* (2018.01)
*A01H 6/82* (2018.01)

(52) U.S. Cl.
USPC ..... Plt./356.2
CPC ..... *A01H 6/824* (2018.05)

(58) Field of Classification Search
USPC ..... Plt./356.2
CPC ..... A01H 5/02
See application file for complete search history.

*Primary Examiner* — Kent L Bell
(74) *Attorney, Agent, or Firm* — Weatherly IP Solutions, LLC; James M. Weatherly

(57) ABSTRACT

A new *Petunia* plant particularly distinguished by smaller flower size with a dark violet flower color; medium vigor; and semi-trailing plant habit, is disclosed.

1 Drawing Sheet

Genus and species: *Petunia hybrida.*
Variety denomination: 'KLEPH23557'.

BACKGROUND OF THE NEW PLANT

The present invention comprises a new and distinct variety of *Petunia*, botanically known as *Petunia hybrida* and hereinafter referred to by the variety name 'KLEPH23557'. 'KLEPH23557' is a selection from a controlled cross between the proprietary female *Petunia* line 'PH-2016-2378' (unpatented) and the commercial male *Petunia* line Potunia® 'Cobalt Blue 2016' (patent status unknown).

In July of 2017, the proprietary female *Petunia* line 'PH-2016-2378' and the male *Petunia* line Potunia® 'Cobalt Blue 2016' were cross pollinated in Latina, Italy and seeds were obtained. The seeds were sown and plants were grown for evaluation. A plant line was selected in April 2018 in Latina, Italy and named 'KLEPH23557'. In May 2018, 'KLEPH23557' was first vegetatively propagated by terminal tip cuttings and tissue culture in Latina, Italy. 'KLEPH23557' was found to reproduce true to type in successive generations of asexual propagation via tissue culture and terminal tip cuttings.

SUMMARY

The following are the most outstanding and distinguishing characteristics of this new variety when grown under normal horticultural practices in Latina, Italy.

1. Small flowers with a dark violet flower color;
2. Medium vigor; and
3. Semi-trailing plant habit.

DESCRIPTION OF THE PHOTOGRAPH

This new *Petunia* plant is illustrated by the accompanying photograph, which shows a close-up of the flower of the plant. The plant is about twelve-week-old grown in Stuttgart, Germany in May 2022. The colors shown are as true as can be reasonably obtained by conventional photographic procedures.

DESCRIPTION OF THE NEW VARIETY

The following detailed descriptions set forth the distinctive characteristics of 'KLEPH23557'. The data which define these characteristics were collected from asexual reproductions carried out in Latina, Italy. Data was collected on sixteen-week-old plants grown indoors in Latina, Italy under greenhouse conditions in April 2024. Color references are to The R.H.S. Colour Chart of The Royal Horticultural Society of London (R.H.S.), 5$^{th}$ edition (2007).

Classification:
- *Family.*—Solanaceae.
- *Species.*—*Petunia hybrida.*
- *Common name.*—*Petunia.*
- *Variety.*—'KLEPH23557'.

Parentage:
- *Female.*—Proprietary *Petunia* line 'PH-2016-2378'.
- *Male.*—Commercial *Petunia* line Potunia® 'Cobalt Blue 2016'.

Plant:
- *Form and habit.*—Medium vigor semi-trailing habit.
- *Height (from top of soil).*—15.0 cm.
- *Width (horizontal plant diameter).*—50.0 cm.
- *Propagation type.*—Vegetative by terminal tip cuttings and tissue culture.
- *Time to produce a finished flowering plant.*—About 10 weeks in winter under short day conditions, about 6.5 weeks in spring.
- *Time to initiate and develop roots.*—2 to 3 weeks.
- *Root description.*—Moderate density, moderate branching, white roots (RHS 155C).

Stems:

*Average number* (*basal*).—7.

*Length of basal branches* (*from the base of the stem to the tip*).—30.0 cm.

*Internode length*.—1.5 cm to 3.0 cm.

*Diameter of branches* (*from midpoint*).—0.2 cm.

*Stem color*.—RHS 138A.

*Anthocyanin*.—Absent.

*Texture*.—Pubescent.

Leaves:

*Arrangement*.—Slightly alternate along the stem and opposite under the inflorescence.

*Length*.—7.0 cm.

*Width*.—3.3 cm.

*Shape*.—Elliptic.

*Apex*.—Slightly obtuse.

*Base*.—Attenuate.

*Margin*.—Entire.

*Immature leaf color*.—Upper surface: RHS 137B. Lower surface: RHS 146B.

*Mature leaf color*.—Upper surface: RHS N137B. Lower surface: RHS 146B.

*Texture*.—Upper surface: Pubescent. Lower surface: Pubescent.

*Venation pattern*.—Arcuate.

*Venation color*.—Upper surface: RHS 137B. Lower surface: RHS 146C.

*Petioles*.—Length: 0.7 cm. Diameter: 0.37 cm. Color: RHS 138B. Texture: Pubescent.

Flower bud:

*Shape*.—Irregularly oblong.

*Length*.—4.5 cm.

*Diameter*.—0.5 cm.

*Color at tight bud*.—RHS N187B.

*Texture*.—Pubescent.

Inflorescence:

*Blooming habit* (*flowering season*).—Continuously flowering during spring and summertime.

*Inflorescence type*.—Sympodial, with monochasial growth.

*Number of flowers per node*.—1.

*Lastingness of individual blooms on the plant*.—About 1 week.

*Fragrance*.—Absent.

*Flowers*.—Arrangement: Composed of 5 petals fused at the base. Diameter (flower face): 7.0 cm. Depth (total length of flower): 6.5 cm. Throat/Funnel: Length: 3.0 cm. Diameter (at opening): 1.0 cm. Texture: Inner surface: Smooth. Outer surface: Pubescent. Color: Inner surface: RHS 90C. Outer surface: RHS 83A. Petals: Color, mature flower (fully opened): Upper surface: Closest to but darker than RHS N88A. Lower surface: RHS 86B. Apex: Truncate. Base: Fused. Shape: Funnelform. Margin: Entire. Strength of waviness: Weak. Degree of lobation: Medium.

*Calyx arrangement*.—Actinomorphic, composed of 5 sepals.

*Sepals*.—Color: Upper surface: RHS 137A. Lower surface: RHS 137C. Length: 1.5 cm. Width: 0.4 cm. Shape: Linear. Apex: Rounded. Base: Attenuate. Margin: Entire. Texture: Upper surface: Pubescent. Lower surface: Pubescent.

*Pedicels*.—Color: RHS 146A. Length: Up to 4.5 cm. Diameter: 0.15 cm. Texture: Pubescent.

Reproductive organs:

*Stamens*.—Quantity: 5. Shape: Needle with oblong head. Filament: Length: up to 1.5 cm. Diameter: 0.01 cm. Color: RHS 145D. Anther: Shape: Oblong. Color: RHS 194A. Length: 0.25 cm. Diameter: 0.2 cm. Pollen: Color: RHS 96C. Amount: Moderate.

*Pistils*.—Quantity per flower: 1.Length: 2.5 cm. Stigma color: RHS 137C. Style color: RHS 145C.

Fruit and seed set: None observed.

Disease and pest/insect resistance: None observed.

COMPARISON WITH PARENTAL LINES AND KNOWN VARIETY

'KLEPH23557' is a distinct variety of *Petunia*. 'KLEPH23557' is distinguished from its parents as described in Table 1:

TABLE 1

Comparison with Parental Lines

| Characteristic | Subject Variety 'KLEPH23557' | Female parent | Male Parent |
|---|---|---|---|
| Flower color | Dark violet | Magenta purple | Dark purple violet |

'KLEPH23557' is most similar to the commercial *Petunia* plant named 'KLEPH17300' (U.S. Plant Pat. No. 30,559). Differences between the two varieties are described in Table 2:

TABLE 2

Comparison with Similar Variety

| Characteristic | Variety 'KLEPH23557' | Commercial line 'KLEPH17300' |
|---|---|---|
| Flower diameter | 7 cm | Around 7.4 cm |
| Vigor | Medium | Medium high |
| Habit | Semi-trailing | A bit more hanging-trailing than 'KLEPH23557' |

I claim:

1. A new and distinct variety of *Petunia* plant named 'KLEPH23557' as illustrated and described herein.

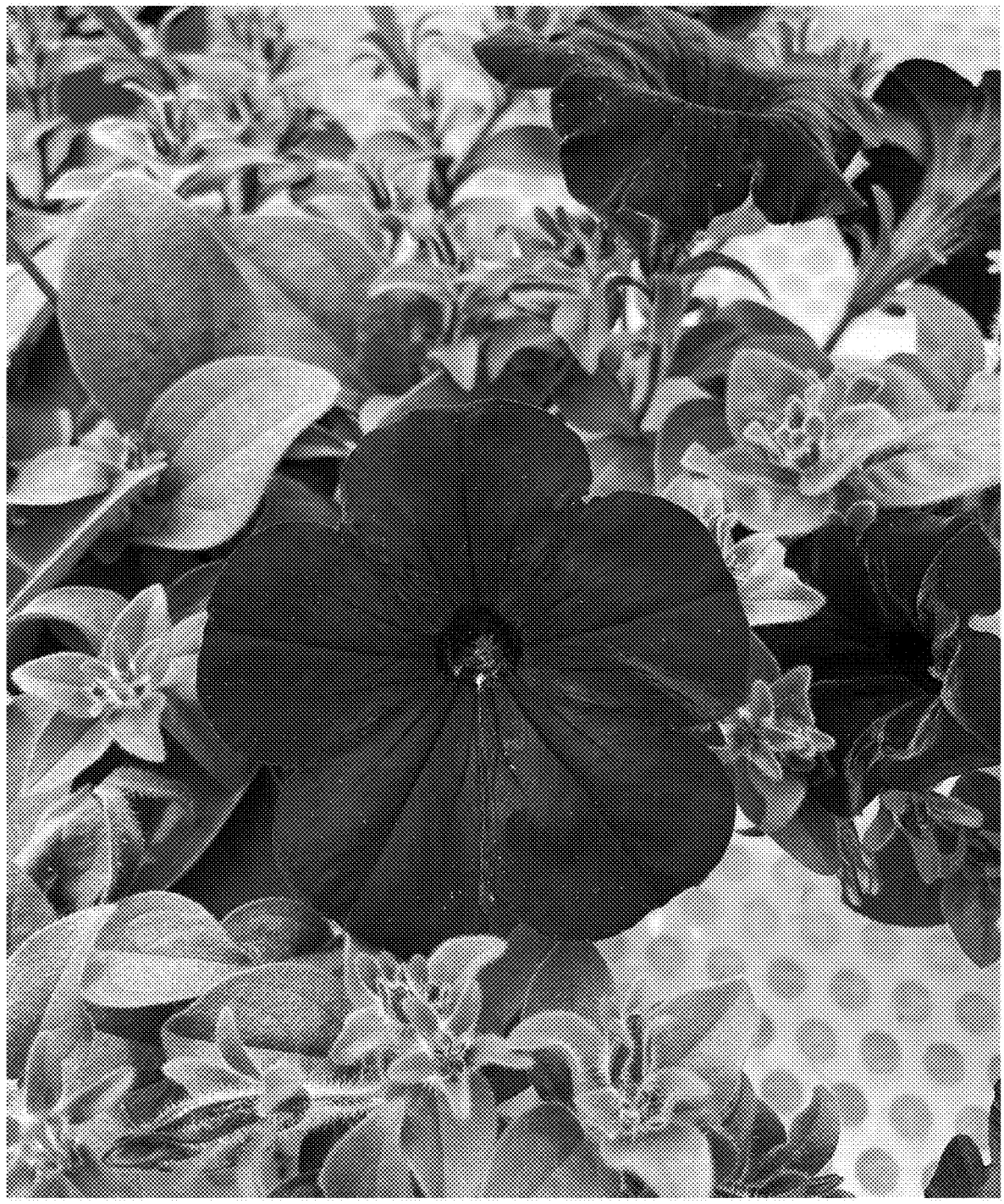

* * * * *